United States Patent
Gronmaier et al.

(10) Patent No.: US 6,388,121 B2
(45) Date of Patent: May 14, 2002

(54) PROCESS FOR THE PRODUCTION OF PHOSPHOR ORGANIC COMPOUNDS

(75) Inventors: Ernst Gronmaier, Allschwil (CH); Peter Staniek, Binzen (DE)

(73) Assignee: Clariant Finance (BVI) Limited, Tortola (VG)

( * ) Notice: Subject to any disclaimer, the term of this patent is extended or adjusted under 35 U.S.C. 154(b) by 0 days.

(21) Appl. No.: 09/896,191

(22) Filed: Jun. 29, 2001

Related U.S. Application Data

(63) Continuation of application No. 09/508,623, filed as application No. PCT/IB99/01479 on Aug. 27, 1999.

(30) Foreign Application Priority Data

| Sep. 1, 1998 | (CH) | 1784/98 |
| Nov. 11, 1998 | (CH) | 2259/98 |

(51) Int. Cl.⁷ ............................................. C07F 9/02
(52) U.S. Cl. ......................................................... 558/95
(58) Field of Search ............................................ 558/95

(56) References Cited

U.S. PATENT DOCUMENTS

| 2,903,475 A | 9/1959 | Harowitz | 260/461 |
| 3,095,351 A | 6/1963 | Godfrey et al. | 167/30 |
| 3,356,775 A | 12/1967 | Mitchell | 260/990 |
| 3,825,629 A | 7/1974 | Hofer et al. | 260/932 |
| 3,901,955 A | 8/1975 | Hofer | 260/927 R |
| 4,764,634 A | 8/1988 | Telschow | 558/96 |
| 5,856,550 A * | 1/1999 | Linhart et al. | 558/71 |
| 6,069,267 A * | 5/2000 | Tam | 558/95 |
| 6,075,159 A * | 6/2000 | Inui et al. | 558/170 |
| 6,077,968 A | 6/2000 | Kleiner | 558/96 |
| 6,278,012 B1 * | 8/2001 | Horold et al. | 558/10 |

OTHER PUBLICATIONS

Michaelis, Ann., 293, 193 (1896).
Kosolapoff, G.M. and Maier, L., Organic Phosphorus Compounds, John Wiley & Sons, New York 1972.
Chemical Abstract No. 119345–01–6.
Chemical Abstract, vol. 126, No. 3, Jan. 20, 1997, abstract No. 031481, Ike T et al. "Preparation of biphenylenediphosphonites as stabilizers for organic materials" XP002123886.
Abstract JP 08 253491 A.

* cited by examiner

Primary Examiner—Deborah C. Lambkin
(74) Attorney, Agent, or Firm—Susan S. Jackson; Scott E. Hanf

(57) ABSTRACT

A novel process is described for preparing phosphonites or phosphinites by reacting a product of a Friedel-Crafts reaction with alcohols or phenols and separating off the byproducts formed. The novelty is the aftertreatment with a protic compound, or with an oxide, hydroxide, (hydrogen) carbonate resp. (hydrogen)phosphate of a metal or with a nitrogen containing compound (as defined in claim 1), or with any combination of one or more substances of the above mentioned compound classes. Products having a low halide and aluminium content are obtained which are distinguished by an improved clear solubility and an improved action as stabilizer for polymeric materials.

4 Claims, No Drawings

PROCESS FOR THE PRODUCTION OF PHOSPHOR ORGANIC COMPOUNDS

This Appn is a con of U.S. application Ser. No. 09/508,623 filed Mar. 10, 2000 which is a 371 of PCT/IB99/01479 Aug. 27, 1999.

FIELD OF THE INVENTION

The invention relates to a process for preparing phosphonites or phosphinites, in particular aromatic phosphonites or phosphinites, having significantly improved properties for stabilizing polymer materials. Products made by this process of the invention are distinguished by higher activity, improved hydrolysis stability and clear solubility as well as a markedly decreased content of unwanted byproducts.

BACKGROUND OF THE INVENTION

As known to those skilled in the art, aromatic phosphonites or phosphinites may be prepared by Friedel-Crafts reaction (reaction 1) of aromatics with halogen-containing phosphorous compounds such as phosphorus trichloride, phosphorus tribromide resp. alkyl- or aryidihalophosphines. The aluminium halide adducts initially formed are cleaved by recomplexing with tertiary amines or phosphoryl chloride by methods known from the literature (reaction 1a). In a subsequent reaction (reaction 2) of the resultant aryldihalophosphines, alkylarylhalophosphines or diarylhalophosphines with alcohols or phenols in the presence or absence of inert solvents and/or acid-binding agents such as tertiary amines, for example, the desired phosphonites or phosphinites are obtained. In this case "halogen" is chloride or bromide, but preferably chloride. These reaction paths have long been known and are described in the literature (e.g. Michaelis, Ann., 293, 193 (1896); Kosolapoff, G. M., Organic Phosphorus Compounds, John Wiley & Sons, New York, 1972). The reaction diagrams below also explicitly include a multiplicity of reactions of types 1 and 2 on one aromatic substrate, e.g. the Friedel-Crafts reaction of diphenyl with 2 equivalents of phosphorus trichloride. The individual reaction partners can be used in this case in a deficiency, stoichiometrically or in excess amounts. Reactions of this type are described, for example, in GB Patent 1372528.

Reaction 1

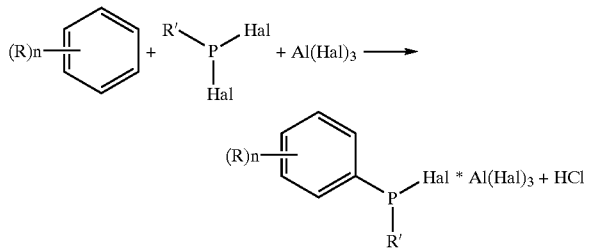

Reaction 1a

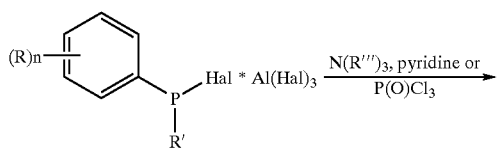

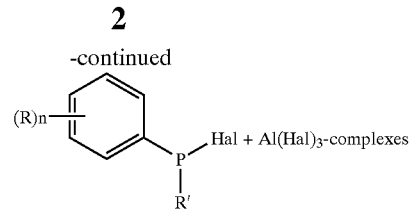

Reaction 2 a) in the presence of an acid acceptor:

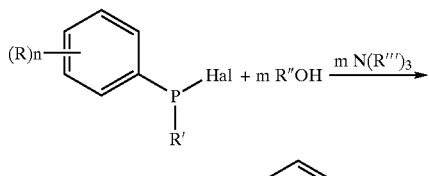

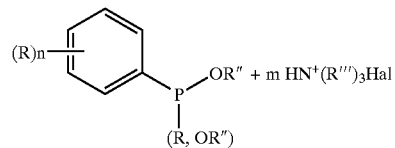

b) without use of an acid acceptor:

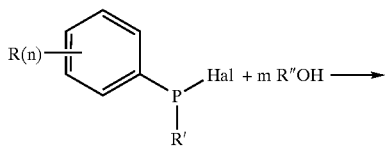

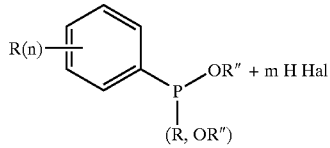

where independently of one another, each group
- R is an aliphatic, cycloaliphatic or aromatic organic radical having 1–36 carbon atoms, which can also contain hetero atoms (N, O, P, S)
- R' is Hal or R;
- R" is an aliphatic, cycloaliphatic or aromatic organic radical having 1–36 carbon atoms, which can also contain hetero atoms (N, O, P, S);
- R''' is an aliphatic, cycloaliphatic or aromatic organic radical having 1–36 carbon atoms, which can also contain hetero atoms (N, O, P, S), or $N(R''')_3$ as such is pyridine or alkyl-substituted pyridine;
- Hal is Cl or Br
- n is 0–5
- m is equal to 1 if R'=R and m is equal to 2 if R'=Hal.

The said reaction mixtures may, under some circumstances, also further comprise organic or organophosphorus compounds such as phenols, alcohols, amines or phosphites, phosphonates, phosphates etc. which are likewise formed during the phosphonite/phosphinite synthesis, remain in the mixture as excess at the end of the reaction or else are deliberately added.

The reaction of Friedel-Crafts reaction products with alcohols or phenols to form phosphonites or phosphinites takes place either without solvent, in the presence of an inert non-polar solvent (such as aliphatics, cycloaliphatics or mixtures thereof), or alternatively without, with stoichiometric or superstoichiometric amounts of an acid acceptor (see reaction 2a).

Common to all these preparation processes is the fact that a certain proportion of unwanted byproducts is present, which byproducts result, for example, from the incomplete reaction of the halophosphorus compounds or are due to residual small amounts of aluminium halide or amine hydrohalide salts. According to the classical procedure, these must be removed by complex and cost-intensive purification processes, such as crystallization, distillation, filtration processes or membrane processes or ion exchange, if a pure product is to be obtained. If these byproduct salts remain in the product, its properties and the usability as polymer stabilizer may be impaired. Thus, the clear solubility, particularly in nonpolar solvents, or else the transparency of the polymers, is decreased, an increase in the corrosivity to metals, promoted by halide ions, can occur and unwanted decomposition processes, such as the hydrolysis of the compounds themselves or of hydrolysable polymers such as polyester or polycarbonate can also be promoted.

SUMMARY OF THE INVENTION

The object of the invention is to decrease significantly the content of unwanted byproducts in a simple and cost-effective manner and at the same time to increase the amount of active substance.

It has surprisingly been found that, after the preparation as described above of the reaction mixtures comprising phosphonites and/or phosphinites, the addition of a small amount of one or more protic compounds such as alcohols, ammonia, primary or secondary amines or water alone or, preferably, in combination with an oxide, hydroxide, (hydrogen)carbonate or (hydrogen)phosphate of a metal and subsequent simple separation of only a small amount of solids after a suitable reaction time leads to a significant decrease in the halide contents, an improvement in the clear solubility in nonpolar solvents, a decrease in the aluminium content and an improved action as stabilizer for polymer materials compared with a phosphonite/phosphinite according to the prior art.

Alternatively, a small amount of one or more nitrogen containing substances of the group consisting of carbonic acid amides, thiocarbonic acid amides, carbonic acid imides, thiocarbonic acid imides, lactames, thiolactames, carbonic acid hydrazides, urea, thiourea, symmetrically and asymmetrically substituted urea and thiourea derivatives, urethanes, uretimides as well as guanidine and its salts or melamine and derivatives thereof, including polymeric compounds of all named classes, or an oxide, hydroxide, (hydrogen)carbonate or (hydrogen)phosphate of a metal may be used alone or, preferably, in combination with a protic compound as defined above and leads to a similar result as described above.

Furthermore, combinations of one or more protic compounds and/or of one or more nitrogen containing substances (all as defined above) with an oxide, hydroxide, (hydrogen)carbonate or (hydrogen)phosphate of a metal can be used to improve the properties of phosphonites/phosphinites as described above.

DETAILED DESCRIPTION OF THE INVENTION

The invention therefore relates to a process for preparing phosphonites or phosphinites of the general formula (I)

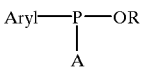
(I)

where
  aryl is a substituted or unsubstituted aryl or heteroaryl radical;
  R is any organic radical having 1–36 carbon atoms, which can also contain hetero atoms; and
  A is either R or OR,
by reacting a product of a Friedel-Crafts reaction of the general formula (II)

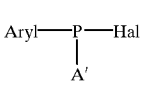
(II)

where
  aryl has the meaning above;
  Hal is halogen; and
  A' is either Hal or R,
with a compound of the general formula (III)

where R has the meaning above, and separating off the byproducts formed, characterized in that an aftertreatment is carried out with a protic compound such as alcohols, ammonia, primary or secondary amines or water, or with an oxide, hydroxide, (hydrogen)carbonate or (hydrogen) phosphate of a metal, or with a nitrogen containing compound of the group consisting of carbonic acid amides, thiocarbonic acid amides, carbonic acid imides, thiocarbonic acid imides, lactames, thiolactames, carbonic acid hydrazides, urea, thiourea, symmetrically and asymmetrically substituted urea and thiourea derivatives, urethanes, uretimides as well as guanidine and its salts or melamine and derivatives thereof, including polymeric compounds of all named classes, or in any combination of one or more substances of the above mentioned compound classes, in the absence of solvent or in an inert, nonpolar solvent and the resultant byproducts are again separated off.

The reaction with the agents of the invention takes place either in the absence of solvent or in inert, nonpolar solvents such as alkanes or aromatics (e.g. benzene, toluene, xylenes, pyridine) or their mixtures, but particularly preferably in alkanes (e.g. heptane, cyclohexane, isooctane, decalin), alkane mixtures (e.g. boiling-point fractions of petroleum ethers) or technical-grade alkane mixtures having only a low content of aromatics. The previously preferred use of chloroaromatics, such as chlorobenzene or dichlorobenzene, as solvent can be avoided by the process described.

The described procedure gives considerable simplifications in the removal of the byproducts, since these, together with the auxiliary agents, are produced only in small amounts and in readily removable form.

Preferably, agent mixtures of alcohols or water together with oxides, hydroxides or carbonates of alkali and alkaline earth metals and of zinc or with a nitrogen containing compound are used in the workup of phosphonites/phosphinites, in which case other compounds such as phosphites, phenols and amines can also be present.

Particular preference is given to the use of mixtures of water and oxides or hydroxides of the alkali and alkaline earth metals or a nitrogen containing compound, selected from the group of carbonic acid amides, imides, lactames, urea, thiourea, substituted urea, melamine and its derivatives as well as polymeric compounds of all these classes, in the workup of aromatic phosphonites/phosphinites, in which case other compounds such as phosphites, phenols and amines can also be present.

Very particular preference is given to the use of mixtures of water and oxides of magnesium or calcium and also hydroxides of sodium, potassium, magnesium and calcium or carbonic acid amides, urea or melamine in the workup of aromatic phosphonites/phosphinites in the presence of compounds such as phosphites, phenols and amines.

The amounts used are 0.1–50 mol % of the protic compound, with respect to the amount of phosphonite/phosphinite, and 0.1–50 mol % of the oxides, hydroxides, (hydrogen)carbonates or phosphates of a metal or of the nitrogen containing compound.

Preferred amounts are 0.5–35 mol % of the protic compound, with respect to the amount of phosphonite/phosphinite, and 0.5–35 mol % of the oxides, hydroxides, (hydrogen)carbonates or phosphates of metals of main groups I, II and III of the Periodic Table of the Elements and of zinc or of the nitrogen containing compound.

Particularly preferred amounts are 1–25 mol % of the protic compound, with respect to the amount of phosphonite/phosphinite, and 1–25 mol % of the oxides or hydroxides of metals of main groups I and II of the Periodic Table of the Elements or 5–30 mol % of the nitrogen containing compound.

The invention is especially suitable for working up a reaction mixture based on the reaction product of 2,4-di-tert-butylphenol with the Friedel-Crafts reaction product of diphenyl and phosphorus trichloride (cf. in this context Chemical Abstracts Number [119345-01-6]; trade name Sandostab® P-EPQ®).

A further possibility consists in the aftertreatment with a combination of a nitrogen containing compound, a protic compound and an oxide, hydroxide, (hydrogen)carbonate or (hydrogen)phosphate of a metal. Preferred compounds are those of alkali and earth alkali metals and zinc. The amounts of such combination to be used are 0.1–50 mol %, preferably 0.5–35 mol %, most preferably 1–25 mol % with respect to the amount of phosphonite/phosphinite.

The phosphonites or phosphinites obtained by the process of the invention are distinguished by a significant lowering of the halide contents, an improvement in the clear solubility in nonpolar solvents, a decrease in the aluminium content and an improved action as stabilizer for polymer materials. Compared with phosphonites or phosphinites of the prior art, which have a content of chloride or hydrolysable chlorine of at least 0.8%, determined by argentometric titration, the phosphonites or phosphinites of the invention have a content of less than 0.5%, in the particularly pure form, of less than 0.3%. The aluminium content, determined by the AES/ICP (atomic emission spectroscopy/inductively coupled plasma) method, is in each case at least 800 ppm or less than 500 ppm, respectively. The clear solubility in nonpolar solvents can be measured by means of turbidity in a 10% strength solution in isooctane.

The resultant phosphonites or phosphinites which are improved in their properties, or their mixtures with other compounds already mentioned above, may be used for stabilizing polymer materials. Polymer materials which may be mentioned are as follows:

1. Polymers of mono- and diolefins, for example polypropylene, polyisobutylene, polybut-1-ene, poly-4-methylpent-1-ene, polyisoprene or polybutadiene and polymers of cycloolefins such as cyclopentene or norbornene; in addition polyethylene (which may optionally be crosslinked), e.g. high-density polyethylene (HDPE), low-density polyethylene (LDPE), linear low-density polyethylene (LLDPE), branched low-density polyethylene (BLDPE). Polyolefins, i.e. polymers of monoolefins, in particular polyethylene and polypropylene, can be prepared by various processes, especially by the following methods:
   a) free-radical (usually at high pressure and high temperature).
   b) by means of a catalyst, where the catalyst usually comprises one or more metals of groups IVb, Vb, VIb or VIII. These metals usually have one or more ligands such as oxides, halides, alkoxides, esters, ethers, amines, alkyls, alkenyls and/or aryls, which can be either -π- or α-coordinated. These metal complexes can be free or fixed to supports, such as on activated magnesium chloride, titanium chloride, aluminium oxide or silicon oxide. These catalysts can be soluble or insoluble in the polymerization medium. The catalysts can be active as such in the polymerization, or other activators can be used, for example metal alkyls, metal hydrides, metal alkylhalides, metal alkyloxides or metal alkyloxanes, the metals being elements of Groups Ia, IIa and/or IIIa. The activators can be modified, for example, with further ester, ether, amine or silyl ether groups. These catalyst systems are usually termed Phillips, Standard Oil Indiana, Ziegler (Natta), TNZ (DuPont), metallocene or single site catalysts (SSC).

2. Mixtures of the polymers mentioned under 1), for example mixtures of polypropylene with polyisobutylene, polypropylene with polyethylene (for example PP/HDPE, PP/LDPE) and mixtures of different types of polyethylene (for example LDPE/HDPE).

3. Copolymers of mono- and diolefins with one another or with other vinyl monomers, for example ethylene-propylene copolymers, linear low-density polyethylene (LLDPE) and mixtures thereof with low-density polyethylene (LDPE), propylene-but-1-ene copolymers, propylene-isobutylene copolymers, ethylene-but-1-ene copolymers, ethylene-hexene copolymers, ethylene-methylpentene copolymers, ethylene-heptene copolymers, ethylene-octene copolymers, propylene-butadiene copolymers, iso-butylene and isoprene copolymers, ethylene-alkyl acrylate copolymers, ethylene-alkyl methacrylate copolymers, ethylene-vinyl acetate copolymers and their copolymers with carbon monoxide or ethylene-acrylic acid copolymers and their salts (ionomers), as well as terpolymers of ethylene with propylene and a diene such as hexadiene, dicyclopentadiene or ethylidene-norbornene; in addition mixtures of such copolymers with one another and with polymers mentioned under 1), for example polypropylene/ethylene-propylene copolymers, LDPE-ethylene-vinyl acetate copolymers, LDPE/ethylene-acrylic acid copolymers, LLDPE/ethylene-vinyl acetate copolymers, LLDPE/ethylene-acrylic acid copolymers and alternating or random polyalkylene-carbon monoxide copolymers and mixtures thereof with other polymers, for example polyamides.

4. Hydrocarbon resins (for example $C_5$–$C_9$) including hydrogenated modifications thereof (e.g. tackifier resins) and mixtures of polyalkylenes and starch.

5. Polystyrene, poly(p-methylstyrene), poly(α-methylstyrene).

6. Copolymers of stynene or α-methylstyrene with dienes or acrylic derivatives, for example styrene-butadiene, styrene-acrylonitrile, styrene-alkyl methacrylate, styrene-butadiene-alkyl acrylate, styrene-butadiene-alkyl methacrylate, styrene-maleic anhydride, styrene-acrylonitrile-methylacrylate; mixtures of high impact strength of styrene copolymers and another polymer, for example a polyacrylate, a diene polymer or an ethylene-propylene-diene terpolymer; and block copolymers of styrene, such as styrene-butadiene-styrene, styrene-isoprene-styrene, styrene-ethylene/butylene-styrene or styrene-ethylene/propylene-styrene.

7. Graft copolymers of styrene or α-methylstyrene, for example styrene on polybutadiene, styrene on polybutadiene-styrene or polybutadiene-acrylon-itrile copolymers, styrene and acrylonitrile (or methacrylonitrile) on polybutadiene; styrene, acrylonitrile and methyl methacrylate on polybutadiene; styrene and maleic anhydride on polybutadiene; styrene, acrylonitrile and maleic anhydride or maleimide on polybutadiene; styrene and maleimide on polybutadiene; styrene and alkyl acrylates or alkyl methacrylates on polybutadiene, styrene and acrylonitrile on ethylene-propylene-diene terpolymers. Styrene and acrylonitrile on polyalkyl acrylates or polyalkyl methacrylates, styrene and acrylonitrile on acrylate-butadiene copolymers, as well as mixtures thereof with the copolymers mentioned under 6), for example as known as ABS, MBS, ASA or AES polymers.

8. Halogen-containing polymers, such as polychloroprene, chlorinated rubber, chlorinated or sulphochlorinated polyethylene, copolymers of ethylene and chlorinated ethylene, epichlorohydrin homo- and copolymers, especially polymers of halogen-containing vinyl compounds, for example polyvinyl chloride, polyvinylidene chloride, polyvinyl fluoride, polyvinylidene fluoride; as well as copolymers thereof such as vinyl chloride-vinylidene chloride, vinyl chloride-vinyl acetate or vinylidene chloride-vinyl acetate.

9. Polymers derived from α,β-unsaturated acids and derivatives thereof, such as polyacrylates and polymethacrylates, polymethyl methacrylates, polyacrylamides and polyacrylonitriles impact-modified with butyl acrylate.

10. Copolymers of the monomers mentioned under 9) with one another or with other unsaturated monomers, for example acrylonitrile-butadiene copolymers, acrylonitrile-alkyl acrylate copolymers, acrylonitrile-alkoxyalkyl acrylate copolymers, acrylonitrile-vinyl halide copolymers or acrylonitrile-alkyl methacrylate-butadiene terpolymers.

11. Polymers derived from unsaturated alcohols and amines or the acyl derivatives or acetals thereof, such as polyvinyl alcohol, polyvinyl acetate, polyvinyl stearate, polyvinyl benzoate, polyvinyl maleate, polyvinyl butyral, polyallyl phthalate or polyallyl melamine; as well as their copolymers with olefins mentioned in section 1.

12. Homopolymers and copolymers of cyclic ethers, such as polyalkylene glycols, polyethylene oxide, polypropylene oxide or copolymers thereof with bisglycidyl ethers.

13. Polyacetals such as polyoxymethylene and those polyoxymethylenes which contain comonomers, for example ethylene oxide; polyacetals modified with thermoplastic polyurethanes, acrylates or MBS.

14. Polyphenylene oxides and polyphenylene sulphides, and mixtures thereof with styrene polymers or polyamides.

15. Polyurethanes derived from hydroxyl-terminated polyethers, polyesters and polybutadienes on the one hand and aliphatic or aromatic polyisocyanates on the other, as well as precursors thereof.

16. Polyamides and copolyamides derived from diamines and dicarboxylic acids and/or from aminocarboxylic acids or the corresponding lactams, such as nylon 4, nylon 6, nylon 6/6, 6/10, 6/9, 6/12, 4/6, 12/12, nylon 11 and nylon 12, aromatic polyamides starting from m-xylene, diamine and adipic acid; polyamides prepared from hexamethylenediamine and isophthalic and/or terephthalic acid and with or without an elastomer as modifier, for example poly-2,4,4-trimethylhexamethylene terephthalamide or poly-m-phenylene isophthalamide, block copolymers of the aforementioned polyamides with polyolefins, olefin copolymers, ionomers or chemically bonded or grafted elastomers; or with polyethers, e.g. with polyethylene glycol, polypropylene glycol or polytetramethylene glycol. In addition, polyamides or copolyamides modified with EPDM or ABS, and polyamides condensed during processing ("RIM polyamide systems").

17. Polyureas, polyimides, polyamide-imides, and polybenzimidazoles.

18. Polyesters derived from dicarboxylic acids and dialcohols and/or from hydroxycarboxylic acids or the corresponding lactones, such as polyethylene terephthalate, polylbutylene terephthalate, poly-1,4-dimethylolcyclohexane terephthalate, polyhydroxybenzoates, as well as block polyether esters derived from hydroxyl-terminated polyethers; in addition, polyesters modified with polycarbonates or MBS.

19. Polycarbonates and polyester carbonates.

20. Polysulphones, polyether sulphones and polyether ketones.

21. Crosslinked polymers derived from aldehydes on the one hand and phenols, urea or melamine on the other hand, such as phenol-formaldehyde resins, urea-formaldehyde resins and melamine-formaldehyde resins.

22. Drying and non-drying alkyd resins.

23. Unsaturated polyester resins derived from copolyesters of saturated and unsaturated dicarboxylic acids with polyhydric alcohols and vinyl compounds as crosslinking agents, and also halogen-containing low-flammability modifications thereof.

24. Crosslinkable acrylic resins derived from substituted acrylates, for example from epoxy acrylates, urethane acrylates or polyester acrylates.

25. Alkyd resins, polyester resins and acrylate resins crosslinked with melamine resins, urea resins, polyisocyanals or epoxy resins.

26. Crosslinked epoxy resins derived from polyepoxides, for example from bis-glycidyl ethers or from cycloaliphatic diepoxides.

27. Natural polymers such as cellulose, natural rubber, gelatin and derivatives thereof which have been chemically modified in a polymer-homologous manner, for example cellulose acetates, cellulose propionates and cellulose butyrates, or the cellulose ethers such as methyl cellulose; as well as rosins and derivatives.

28. Mixtures (polyblends) of the aforementioned polymers, for example PP/EPDM, polyamide/EPDM or ABS, PVC/EVA, PVC/ABS, PVC/MBS, PC/ABS, PBTP/ABS, PC/ASA, PC/PBT, PVC/CPE, PVC/acrylates, POM/thermoplastic PUR, PC/thermoplastic PUR, POM/acrylate, POM/MBS, PPO/HIPS, PPO/PA 6.6 and copolymers, PA/HDPE, PA/PP, PA/PPO.

29. Natural and synthetic organic substances which constitute pure monomeric compounds or mixtures thereof, for example mineral oils, animal or vegetable fats, oils and waxes, or oils, waxes and fats based on synthetic esters (e.g. phthalates, adipates, phosphates or trimellitates), and also blends of synthetic esters with mineral oils in any desired proportion by weight, as are employed, for example, as spin finishes, and aqueous emulsions thereof.

30. Aqueous emulsions of natural or synthetic rubbers, such as natural rubber latex or latices of carboxylated styrene-butadiene copolymers.

In these polymers, further additives may be present, for example:

1. Antioxidants 1.1 Alkylated monophenols, for example 2,6-di-tert-butyl-4-methylphenol, 2-butyl-4,6-dimethylphenol, 2,6-di-tert-butyl-4-ethylphenol, 2,6-di-tert-butyl-4-n-butylphenol, 2,6-di-tert-buytl-4-isobutylphenol, 2,6-dicyclopentyl-4-methylphenol, 2-($\alpha$-methylcyclohexyl)-4,6-dimethylphenol, 2,6-dioctadecyl-4-methylphenol, 2,4,6-tricyclohexylphenol, 2,6-di-tert-butyl-4-methoxymethylphenol, 2,6-dinonyl-4-methylphenol, 2,4-dimethyl-6-(1'-methylundec-1'-yl) phenol, 2,4-dimethyl-6-(1'-methylheptadecyl)phenol, 2,4-dimethyl-6-(1'-methyltridec-1'-yl)phenol and mixtures thereof.

1.2 Alkylthiomethylphenols, for example 2,4-dioctylthiomethyl-6-tert-butylphenol, 2,4-dioctylthiomethyl-6-methylphenol, 2,4-dioctylthiomethyl-6-ethylphenol, 2,6-di-dodecyl-thiomethyl-4-nonylphenol.

1.3 Hydroquinones and alkylated hydroquinones, for example 2,6-di-tert-butyl-4-methoxyphenol, 2,5-di-tert-butylhydroquinone, 2,5-di-tert-amylhydroquinone, 2,6-diphenyl-4-octadecyloxyphenol, 2,6-di-tert-butylhydroquinone, 2,5-di-tert-butyl--4-hydroxy-anisole, 3,5-di-tert-butyl-4-hydroxyanisole, 3,5-di-lert-butyl-4-hydroxyphenyl stearate, bis(3,5-di-tert-butyl-4-hydroxyphenyl) adipate.

1.4 Tocopherols, for example $\alpha$-tocopherol, $\beta$-tocopherol, $\gamma$-tocopherol, $\delta$-tocopherol and mixtures thereof (vitamin E).

1.5 Hydroxylated thiodiphenyl ethers, for example 2,2'-thiobis(6-tert-butyl-4-methylphenol), 2,2'-thiobis(4-octylphenol), 4,4'-thiobis(6-tert-butyl-3-methylphenol), 4,4'-thiobis(6-tert-butyl-2-methylphenol), 4,4'-thiobis(3,6-di-sec-amylphenol), 4,4'-bis(2,6-dimethyl-4-hydroxyphenyl) disulphic.

1.6 Alkylidenebisphenols, for example 2,2'-methylenebis(6-tert-butyl-4-methylphenol), 2,2'-methylenebis(6-tert-butyl-4-ethylphenol), 2,2'-methylenebis[4-methyl-6-($\alpha$-methyl-cyclohexyl)phenol], 2,2'-methylenebis(4-methyl-6-cyclohexylphenol), 2,2'-methylene-bis(6-nonyl-4-methylphenol), 2,2'-methylenebis(4,6-di-tert-butylphenol), 2,2'-ethylidene-bis(4,6-di-tert-butylphenol), 2.2'-ethylidenebis(6-tert-butyl-4-isobutylphenol), 2,2'-methylenebis[6-($\alpha$-methylbenzyl)-4-nonylphenol], 2,2'-methylenebis[6-($\alpha$,$\alpha$-dimethylbenzyl)-4-nonylphenol], 4,4'-methylenebis(2,6-di-tert-butylphenol), 4,4'-methylenebis(6-tert-bulyl-1-2-methylphenol), 1,1-bis(5-tert-butyl-4-hydroxy-2-methylphenyl)butane, 2,6-bis(3-tert-butyl-5-methyl-2-hydroxybenzyl)4-methylphenol, 1,1,3-tris(5-tert-butyl-4-hydroxy-2-methylphenyl)butane, 1,1-bis(5-tert-butyl-4-hydroxy-2-methylphenyl)-3-n-dodecyl-mercaptobutane, ethylene glycol bis[3,3-bis'(3'-tert-butyl-4'-hydroxyphenyl)butyrate], bis(3-tert-butyl-4-hydroxy-5-methylphenyl)dicyclopentadiene, bis[2-(3'-tert-butyl-2'-hydroxy-5'-methylbenzyl)-6-tert-butyl-4-methylphenyl] terephthalate, 1,1-bis(3,5-di-methyl-2-hydroxyphenyl) butane, 2,2-bis(3,5-di-tert-butyl-4-hydroxyphenyl)propane, 2,2-bis(5-tert-butyl-4-hydroxy-2-methylphenyl)-4-n-dodecylmercaptobutane, 1,1,5,5-tetra-(5-tert-butyl4-hydroxy-2-methylphenyl)pentane.

1.7 O-, N- and S-benzyl compounds, for example 3,5,3',5'-tetra-tert-butyl-4,4'-dihydroxydibenzyl ether, octadecyl-4-hydroxy-3.5-dimethylbenzyl mercaptoacetate, tris(3,5-di-tert-butyl-4-hydroxybenzyl)amine, bis(4-tert-butyl-3-hydroxy-2,6-dimethyl-benzyl) dithioterephthalate, bis(3,5-di-tert-butyl-4-hydroxybenzyl) sulphide, isooctyl 3,5-di-tert-butyl-4-hydroxybenzyl mercaptoacetate.

1.8 Hydroxybenzylated malonates, for example dioctadecyl 2,2-bis(3,5-di-tert-butyl-2-hydrorybenzyl)malonate, dioctadecyl 2-(3-tert-butyl-4-hydroxy-5-methylbenzyl)-malonate, didodecyl mercaptoethyl-2,2-bis(3,5-di-tert-butyl4-hydroxybenzyl)malonate, di[4-(1,1,3,3-tetramethylbutyl)phenyl], 2,2-bis(3,5-di-tert-butyl-4-hydroxybenzyl)malo-nate.

1.9 Aromatic hydroxybenzyl compounds, for example 1,3,5-tris(3,5-di-tert-buty)-4-hydroxybenzyl)-2,4,6-trimethylbenzene, 1,4-bis(3,5-di-tert-butyl-4-hydroxybenzyl)-2,3,5,6-tetramethylbenzene, 2,4,6-tris(3,5-di-tert-buryl-4-hydroxybenzyl)phenol.

1.10 Triazine compounds, for example 2,4-bis-octylmercapto-6-(3,5-di-tert-butyl-4-hydroxyanilino)-1,3,5-triazine, 2-octylmercapto-4,6-bis(3,5-di-tert-butyl-4-hydroxy-anilino)-1,3,5-triazine, 2-octyl-mercapto4,6-bis(3,5-di-tert-butyl-4-hydroxyphenoxy)-1,3,5-triazine, 2,4,6-tris(3,5-di-tert-butyl-4-hydroxyphenoxy)-1,2,3-triazine, 1,3,5-tris-(3,5-di-tert-butyl-4-hydroxybenzyl) isocyanurate, 1,3,5-tris(4-tert-butyl-3-hydroxy-2,6-dimethylbenzyl) isocyanurate, 2,4,6-tris(3,5-di-tert-butyl-4-hydroxyphenylethyl)-1,3,5-triazine, 1,3,5-tris(3,5-di-tert-butyl-4-hydroxyphenylpropionyl)hexahydro-1,3,5-triazine, 1,3,5-tris(3,5-dicyclohexyl-4-hydroxybenzyl) isocyanurate.

1.11 Benzylphosphonates, for example dimethyl 2,5-di-tert-butyl-4-hydroxybenzylphosphonate diethyl 3,5-di-tert-butyl-4-hydroxybenzylphosphonate, dioctadecyl 3,5-di-tert-butyl-4-hydroxybenzylphosphonate, dioctadecyl 5-tert-butyl-4-hydroxy-3-methyl-benzylphosphonate, the Ca salt of the monoethyl ester of 3,5-di-tert-butyl-4-hydroxybenzylphosphonic acid.

1.12 Acylaminophenols, 4-hydroxylauramide, 4-hydroxystearanilide, octyl N-(3,5-di-tert-butyl-4-hydroxyphenyl)carbamate.

1.13 Esters of $\beta$-(3,5-di-tert-butyl-4-hydroxyphenyl) propionic acid with mono- or polyhydric alcohols, e.g. with methanol, ethanol, octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl) isocyanurate, N,N'-bis(hydroxyethyl)oxalamide, 3-thiaundecanol, 3-thiapentadecanol, trimethyl-hexanediol, trimethylolpropane, 4-hydroxymethyl-1-phospha-2,6,7-trioxabicyclo-[2.2.2]octane.

1.14 Esters of $\beta$-(5-tert-butyl-4-hydroxy-3-methylphenyl) propionic acid with mono- or polyhydric alcohols, e.g. with methanol, ethanol, octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl) isocyanurate, N,N'-bis(hydroxyethyl)oxalamide, 3-thiaundecanol, 3-thiapentadecanol, trimethylhexanediol, trimethylolpropane, 4-hydroxymethyl-1-phospha-2,6,7-trioxabi-cyclo[2.2.2]octane.

1.15 Esters of $\beta$-(3,5-dicyclohexyl-4-hydroxy-phenyl) propionic acid with mono- or polyhydric alcohols, e.g. with methanol, ethanol, octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl) isocyanurate, N,N'-bis(hydroxyethyl)oxalamide, 3 thiaundecanol, 3-thiapentadecanol, trimethyl-hexanediol, trimethylolpropane, 4-hydroxymethyl-1-phospha-2,6,7-trioxabicyclo-[2.2.2]octane.

1.16 Esters of 3,5-di-tert-butyl-4-hydroxyphenylacetic acid with mono- or polyhydric alcohols, e.g. with methanol, ethanol, octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl) isocyanurate, N,N-bis-(hydroxyethyl)oxalamide, 3-thiaundecanol, 3-thiapentadecanol, trimethyl-hexanediol, trimethylolpropane, 4-hydroxymethyl-1-phospha-2,6,7-trioxabicyclo-[2.2.2]octane.

1.17 Amides of β-(3,5-di-tert-butyl-4-hydroxy-phenyl) propionic acid, e.g. N,N'-bis(3,5-di-tert-butyl4-hydroxyphenylpropionyl)hexamethylenediamine, N,N'-bis(3,5-di-tert-butyl-4-hydroxyphenylpro-pionyl) trimethylenediamine, N,N'-bis(3,5-di-tert-butyl-4-hydroxy-phenylpropionyl)hydrazine.

2. UV Absorbers and Light Stabilizers 2.1 2-(2'-Hydroxyphenyl)benzotriazoles, for example 2-(2'-hydroxy-5'-methylphenyl)benzotriazole, 2-(3',5'-di-tert-butyl-2'-hydroxyphenyl)benzotriazole, 2-(5'-tert-butyl-2'-hydroxyphenyl)benzotriazole, 2-(2'-hydroxy-5'-(1,1.3,3-tetramethylbutyl)phenyl)benzo-triazole, 2-(3',5'-di-tert-butyl-2'-hydroxyphenyl)-5-chlorobenzotriazole, 2-(3-tert-butyl-2'- hydroxy-5'-methylphenyl)-5-chlorobenzotriazole, 2-(3'-sec-butyl-5'-tert-butyl-2'-hydroxy-phenyl) benzotriazole, 2-(2'-hydroxy-4'-octoxyphenyl) benzotriazole, 2-(3',5'-di-tert-amyl-2'-hydroxyphenyl) benzotriazole, 2-(3',5'-bis(α,α-dimethylbenzyl-2'-hydroxyphenyl)benzotriazole, a mixture of 2-(3'-tert-butyl-2'-hydroxy-5'-(2-octyloxycarbonylethyl)phenyl-5-chlorobenzotriazole, 2-(3'-tert-butyl-5'-[2-(2-ethylhexyloxy)carbonylethyl]-2'-hydroxyphenyl)-5-chlorobenzotriazole, 2-(3'-tert-butyl-2'-hydroxy-5'-(2-methoxycarbony-lethyl)phenyl)-5-chlorobenzotriazole, 2-(3'-tert-butyl-2'-hydroxy-5'-(2-methoxycarbonyl-ethyl) phenyl)benzotriazole, 2-(3'-tert-butyl-2'-hydroxy-5'-(2-octyloxycarbonylethyl)-phenyl)benzotriazole, 2-(3'-tert-butyl-5'-[2-(2-ethylhexyloxy)carbonylethyl]-2'-hydroxyphenyl)benzotriazole, 2-(3'-dodecyl2'-hydroxy-5'-methylphenyl)benzotriazole and 2-(3'-tert-butyl-2'-hydroxy-5'-(2-isooctyloxycarbonylethyl)phenyl-benzotriazole, 2,2'-methy-lene-bis[4(1,1,3,3-tetramethylbutyl)-6-benzotriazol-2-ylphenol]; the transesterification product of 2-[3-tert-butyl-5'-(2-methoxycarbonylethyl)-2'-hydroxy-phenyl] benzotriazole with polyethylene glycol 300, [R—CH₂CH₂—COO(CH₂)₃]₂ where R=3'-tert-butyl-4'-hydroxy-5'-2H-benzotriazol-2-ylphenyl.

2.2 2-Hydroxybenzophenones, for example the 4-hydroxy, 4-methoxy, 4-octoxy, 4-decyloxy, 4-dodecyloxy, 4-benzyloxy, 4,2',4'-trihydroxy and 2'-hydroxy-4,4'-dimethoxy derivative.

2.3 Esters of substituted or unsubstituted benzoic acids, for example 4-tert-butyl-phenyl salicylate, phenyl salicylate, octylphenyl salicylate, dibenzoylresorcinol, bis(4-tert-butylbenzoyl)resorcinol, benzoylresorcinol, 2,4-di-tert-butylphenyl 3,5-di-tert-butyl-4-hydroxybenzoate, hexadecyl 3,5-di-tert-butyl-4-hydroxybenzoate, octadecyl 3,5-di-tert-butyl-4-hydroxybenzoate, 2-methyl-4,6-di-tert-butyl-phenyl 3,5-di-tert-butyl-4-hydroxy-benzoate.

2.4 Acrylates, for example ethyl α-cyano-β,β-diphenylacrylate or isooctyl α-cyano-β,β-diphenylacrylate, methyl α-carbomethoxycinnamate, methyl α-cyano-β-methyl-p-methoxycinnamate or butyl α-cyano-β-methyl-p-methoxycinnamate, methyl α-carbo-methoxy-p-methoxycinnamate and N-(β-carbomethoxy-β-cyanovinyl)-2-methylindoline.

2.5 Nickel compounds, for example nickel complexes of 2,2'-thio-bis-[4-(1,1,3,3-tetramethylbutyl)phenol], such as the 1:1 or 1:2 complex, with or without additional ligands such as n-butylamine, triethanolamine or N-cyclohexyldiethanolamine, nickel dibutyldithiocarbamate, nickel salts of monoalkyl esters, such as of the methyl or ethyl ester, of 4-hydroxy-3,5-di-tert-butylbenzylphosphonic acid, nickel complexes of ketoximes, e.g. of 2-hydroxy-4-methylphenyl undecyl ketoxime, nickel complexes of 1-phenyl-4-lauroyl-5-hydroxypyrazole, with or without additional ligands.

2.6 Sterically hindered amines, for example bis(2,2,6,6-tetramethylpiperidyl) sebacate, bis(2,2,6,6-tetramethylpiperidyl) succinate, bis(1,2,2,6,6-pentamethylpiperidyl) sebacate, bis(1,2,2,6,6-pentamethylpiperidyl) n-butyl-3,5-di-tert-butyl-4-hydroxybenzyl-malonate, the condensation product of 1-hydroxyethyl-2,2,6,6-tetramethyl-4-hydroxypiperidine and succinic acid, the condensation product of N,N'-bis-(2,2,6,6-tetramethyl-4-piperidyl)-hexamethylenediamine and 4-tert-octylamino-2,6-dichloro-1,3,5-s-triazine, tris-(2,2,6,6-tetramethyl-4-piperidyl) nitrilotriacetate, tetrakis(2,2,6,6-tetramethyl-4-piperidyl) 1,2,3,4-butanetetraoate, 1,1'-(1,2-ethanediyl)-bis-(3,3,5,5-tetramethylpiperazinone), 4-benzoyl-2,2,6,6-tetramethylpiperidine, 4-stearyloxy-2,2,6,6-tetramethylpiperidine, bis(1,2,2,6,6-pentamethylpiperidyl) 2-n-butyl-2-(2-hydroxy-3,5-di-tert-butylbenzyl)malonate, 3-n-octyl-7,7,9,9-tetramethyl-1,3,8-triazaspiro[4.5]de-cane-2,4-dione, bis(1-octyloxy-2,2,6,6-tetramethylpiperidyl) sebacate, bis-(1-octyloxy-2,2,6,6-tetramethylpiperidyl) succinate, the condensation product of N,N'-bis(2,2,6,6-tetramethyl-4-piperidyl) hexamethylenediamine and 4-morpholino-2,6-dichloro-1,3,5-triazine, the condensation product of 2-chloro-4,6-di-(4-n-butylamino-2,2,6,6-tetramethylpiperidyl)-1,3,5-triazine and 1,2-bis-(3-aminopropylamino)ethane, the condensation product of 2-chloro-4,6-di-(4-n-butylamino-1,2,2,6,6-pentamethyl-piperidyl)-1,3,5-triazine and 1,2-bis-(3-aminopropylamino)ethane, 8-acetyl-3-dodecyl-7,7,9,9-tetramethyl-1,3,8-triaz-aspiro[4.5]decane-2,4-dione, 3-dodecyl-1-(2,2,6,6-tetra-methyl-4-piperidyl)pyrrolidine-2,5-dione, 3-dodecyl-1-(1,2,2,6,6-pentamethyl-4-piperi-dyl) pyrrol-idine-2,5-dione.

2.7 Oxalamides, for example 4,4'-dioctyloxyoxanilide, 2,2'-diethoxyoxanilide, 2,2'-dioctyloxy-5,5'-di-tert-butyloxanilide, 2,2'-didodecyloxy-5,5'-di-tert-butyl-oxanilide, 2-ethoxy-2'-ethyloxanilide, N,N'-bis(3-dimethylaminopropyl)-oxalamide, 2-ethoxy-5-tert-butyl-2'-ethyloxanilide and its mixture with 2-ethoxy-2'-ethyl-5,4'-di-tert-butyloxanilide and mixtures of o- and p-methoxy-disubstituted and of o- and p-ethoxy-disubstituted oxanilides.

2.8 2-(2-Hydroxyphenyl)-1,3,5-triazines, for example 2,4,6-tris(2-hydroxy-4-octyloxyphenyl)-1,3,5-triazine, 2-(2-hydroxy-4-octyloxyphenyl)4,6-bis(2,4-dimethylphenyl)-1,3,5-triazine, 2-(2,4-dihydroxy-phenyl)-4,6-bis(2;4-dimethylphenyl)-1,3,5-triazine, 2,4-bis(2-hydroxy-4-propyloxyphenyl)-6-(2,4-dimethylphenyl)-1,3,5-triazine, 2-(2-hydroxy-4-octyloxyphenyl)-4,6-bis(4-methylphenyl)-1,3,5-triazine, 2-(2-hydroxy-4-dodecyloxyphenyl)-4,6-bis(2,4-dimethylphenyl)-1,3,5-triazine, 2-[2-hydroxy-4-(2-hydroxy-3-butyloxytpropyloxy)phenyl]-4,6-bis(2,4-dimethylphenyl)-1,3,5-triazine, 2-[2-hy-droxy-4-(2-hydroxy-3-octyloxypropyloxy)phenyl]-4,6-bis(2,4-dimethylphenyl)-1,3,5-triazine.

3. Metal deactivators, for example, N,N'-diphenyloxalamide, N-salicylal-N'-salicyloylhydrazine, N,N'-bis(salicyloyl)hydrazine, N,N'-bis(3,5-di-tert-butyl-4-hydroxyphenylpropionyl)hydrazine, 3-salicyl-oylamino-1,2,4-triazole, bis(benzylidene)-oxalyl dihydrazide, oxanilide, isophthaloyl dihydrazide, sebacoyl bisphenylhydrazide, N,N'-diacetyladipoyl dihydrazide, N,N'-bis(salicyloyl) oxalyl dihydrazide, N,N'-bis(salicyloyl)thiopropionyl dihydrazide.

4. Phosphites and phosphonites, for example triphenyl phosphite, diphenyl alkyl phosphites, phenyl dialkyl phosphites, tris(nonylphenyl) phosphite, trilauryl phosphite, trioctadecyl phosphite, distearyl pentaerythritol diphosphite, tris(2,4-di-tert-butyl-phenyl) phosphite, diisodecyl pentaerythritol diphosphite, bis(2,4-di-tert-butylphenyl) pentaerythri-tol diphosphite, bis(2,6-di-tert-butyl-4-methylphenyl) pentaerythritol diphosphite, bisisodecyloxy pentaerythritol diphosphite, bis(2,4-di-tert-butyl-6-methylphenyl) pentaerythritol diphosphite, bis(2,4,6-tri-tert-butylphenyl) pentaerythritol diphosphite, tristearyl sorbitol triphosphite, tetrakis(2,4-di-tert-butylphenyl) 4,4'-biphenylenediphosphonite, 6-isooctyloxy-2,4,8,10-tetra-tert-butyl-12H-dibenzo[d,g]-1,3,2-dioxaphosphocin, 6-fluoro-2,4,8,10-tetra-tert-butyl-12-methyl-dibenzo[d,g]-1,3,2-dioxaphosphocin, bis(2,4-di-tert-butyl-6-methylphenyl) methyl phosphite, bis(2,4-di-tert-butyl-6-methylphenyl) ethyl phosphite.

5. Peroxide scavengers, examples being esters of β-thiodipropionic acid, for example the lauryl, stearyl, myristyl or tridecyl ester, mecaptobenzimidazole, the zinc salt of 2-mercaptobenzimidazole, zinc dibutyldithiocarbamate, dioctadecyl disulphide, pentaerythritol tetrakis(β-dodecylmercapto)propionate.

6. Polyamide stabilizers, examples being copper salts in combination with iodides and/or phosphorus compounds and salts of divalent manganese.

7. Basic costabilizers, examples being melamin, polyvinylpyrrolidone, dicyandiamide, triallyl cyanurate, urea derivatives, hydrazine derivatives, amines, polyamides, polyurethanes, alkali metal salts and alkaline earth metal salts of higher fatty acids, for example Ca stearate, Zn stearate, Mg behenate, Mg stearate, Na ricinoleate, K palmitate, antimony pyrocatecholate or tin pyrocatecholate.

8. Nucleating agents, such as benzoic acid, 4-tert-butylbenzoic acid, adipic acid; diphenylacetic acid and their salts, phosphates, phosphonates and phosphinates and their esters and salts or clarifiers, such as derivatives of di-benzylidene sorbitol.

9. Fillers and reinforcing agents, examples being calcium carbonate, silicates, glass fibers, asbestos, talc, kaolin, mica, barium sulphate, metal oxides and hydroxides, carbon black, graphite.

10. Other additives, examples being plasticizers, lubricants, emulsifiers, pigments, optical brighteners, flameproofing agents, antistatics, blowing agents.

These additional additives can be added to the polymers before, together with or after addition of the stabilizers of the invention. These additives and also the stabilizers of the invention can be added in this case as solid, in solution or melt as well as in the form of solid or liquid mixtures or masterbatches/concentrates.

The advantageous action of the compounds prepared according to the invention is to be shown by the examples below, but the applicability to similar areas is not to be restricted by this.

EXAMPLES

PREPARATION EXAMPLE 1 (PRODUCT 1)

The Friedel-Crafts product of 0.16 mol of diphenyl, 0.42 mol of aluminium chloride and 0.35 mol of phosphorus trichloride is added to a solution of 0.63 mol of 2,4-di-tert-butylphenol, 102 ml of pyridine in 220 ml of isooctane. After a reaction time of 2 h at approximately 85° C., 220 ml of isooctane are added to separate off the aluminium complex formed and the resulting product solution is admixed with 0.026 mol of calcium oxide and 0.026 mol of water. The mixture is stirred for 1 h and the solid present is filtered off at room temperature. After taking off the solvent in vacuum, a melt remains which, after it is poured out, solidifies as a pale-yellowish transparent glass.

PREPARATION EXAMPLE 2 (PRODUCT 2)

The Friedel-Crafts product of 0.16 mol of diphenyl, 0.42 mol of aluminium chloride and 0.35 mol of phosphorus trichloride is added to a solution of 0.63 mol of 2,4-di-tert-butylphenol, 102 ml of pyridine in 220 ml of isooctane. After a reaction time of 2 h at approximately 85° C., 220 ml of isooctane are added to separate off the aluminium complex formed and the resulting product solution is admixed with 0.032 mol of calcium hydroxide and 0.032 mol of water. The mixture is stirred for 1 h and the solid present is filtered off at room temperature. After taking off the solvent in vacuum, a melt remains which, after it is poured out, solidifies as a pale-yellowish transparent glass.

PREPARATION EXAMPLE 3 (PRODUCT 3)

The Friedel-Crafts product of 0.16 mol of diphenyl, 0.42 mol of aluminium chloride and 0.35 mol of phosphorus trichloride is added to a solution of 0.63 mol of 2,4-di-tert-butylphenol, 102 ml of pyridine in 220 ml of isooctane. After a reaction time of 2 h at approximately 85° C., 220 ml of isooctane are added to separate off the aluminium complex formed and the resulting product solution is admixed with 0.016 mol of calcium oxide and 0.016 mol of sodium hydroxide solution (30% by weight). The mixture is stirred for 1 h and the solid present is filteredd off at room temperature. After taking off the solvent in vacuum, a melt remains which, after it is poured out, solidifies as a pale-yellowish transparent glass.

PREPARATION EXAMPLE 4 (PRODUCT 4)

The Friedel-Crafts product of 0.16 mol of diphenyl, 0.42 mol of aluminium chloride and 0.35 mol of phosphorus trichloride is added to a solution of 0.63 mol of 2,4-di-tert-butylphenol, 102 ml of pyridine in 220 ml of isooctane. After a reaction time of 2 h at approximately 85° C., 220 ml of isooctane are added to separate off the aluminium complex formed and the resulting product solution is admixed with 0.016 mol of sodium hydroxide solution (30% by weight). The mixture is stirred for 1 h and the solid present is filtered off at room temperature. After taking off the solvent in vacuum, a melt remains which, after it is poured out, solidifies as a pale-yellowish transparent glass.

PREPARATION EXAMPLE 5

The Friedel-Crafts product of 0.16 mol of diphenyl, 0.42 mol of aluminium chloride and 0.35 mol of phosphorus trichloride is added to a solution of 0.63 mol of 2,4-di-tert.butylphenol, 102 ml pyridine in 220 ml iso-octane. After a reaction time of 2 h at approx. 85° C., 220 ml iso-octane are added to separate off the aluminium complex formed and the resulting product solution is admixed with 0.016 mol of urea and 0.008 mol of water. The mixture is stirred for 1 h and the solid present is filtered off at room temperature. After taking off the solvent in vacuum, a melt remains which, after it is poured out, solidifies as a pale-yellowish transparent glass.

PREPARATION EXAMPLE 6

The Friedel-Crafts product of 0.16 mol of diphenyl, 0.42 mol of aluminium chloride and 0.35 mol of phosphorus trichloride is added to a solution of 0.63 mol of 2,4-di-tert.butylphenol, 102 ml pyridine in 220 ml iso-octane. After a reaction time of 2 h at approx. 85° C., 220 ml iso-octane are added to separate off the aluminium complex formed and the resulting product solution is admixed with 0.045 mol of urea. The mixture is stirred for 1 h and the solid present is filtered off at room temperature. After taking off the solvent in vacuum, a melt remains which, after it is poured out, solidifies as a pale-yellowish transparent glass.

PREPARATION EXAMPLE 7

The Friedel-Crafts product of 0.16 mol of diphenyl, 0.42 mol of aluminium chloride and 0.35 mol of phosphorus trichloride is added to a solution of 0.63 mol of 2,4-di-tert-butylphenol, 120 ml pyridine in 220 ml isooctane. After a reaction time of 2 h at approx. 85° C., 220 ml isooctane are added to separate off the aluminium complex formed and the resulting product solution is admixed with 0.0065 mol of calcium oxide and 0.026 mol of water. The mixture is stirred for 1 h and the solid present is filtered off at room temperature. After taking off the solvent in vacuum, a melt remains which, after it is poured out, solidifies as a pale-yellowish transparent glass.

For the use examples below, the comparison product used is a phosphonite, which is commercially available as Sandostab P-EPQ from Clariant Huningue S.A. and is prepared according to GB Patent 1372528, Example 12.

USE EXAMPLE A
Comparison of the Clear Solubilities

10% strength solutions of products 1 to 6 and of the comparison product are prepared by dissolving 10 g of each substance in 90 g of isooctane. The solutions of the products 1 to 6 prepared according to the invention are colorless and transparent, while the solution of the comparison product is opaque and a precipitate is deposited after standing for a short time. As a result, the products of the invention are suitable in particular for adding as homogeneous solutions, additives in homogeneous coatings systems and their prepolymeric components as well as in general for use in transparent end products, such as coatings, powder coatings, polycarbonate, polystyrene, polyethylene terephthalate, polybutylene terephthalate, polyvinyl chloride, polymethylmethacrylate or cyclic olefin copolymers (COC), i.e. any polymeric materials which are present to a high degree in the amorphous state having only small crystalline contents.

USE EXAMPLE B
Comparison of the Chloride Contents

The contents of chloride or hydrolysable chlorine are determined by argentometric titration with potentiometric end point determination of a product suspension in water. For the products 1 to 4 prepared according to the invention, significantly lower chloride contents are found compared with the comparison product:

| Chloride content | Prod. 1 | Prod. 2 | Prod. 3 | Prod. 4 | Prod. 5 | Prod. 6 | Comparison product |
|---|---|---|---|---|---|---|---|
| in % | 0.08 | 0.07 | 0.17 | 0.19 | 0.15 | 0.29 | 0.86 |

This reduction in chloride content by up to an order of magnitude represents a significant improvement over the prior art which can be achieved without a substantial increase in resources and cost-effectively.

USE EXAMPLE C
Comparison of the Aluminium Contents

The contents of aluminium are determined by the method AES/ICP. For the products 1 to 6 prepared according to the invention, significantly lower aluminium contents are found compared with the comparison product:

| aluminium content | Prod. 1 | Prod. 2 | Prod. 3 | Prod. 4 | Prod. 5 | Prod. 6 | Comparison product |
|---|---|---|---|---|---|---|---|
| in ppm | 275 | 330 | 450 | 400 | 250 | 500 | 940 |

This reduction in aluminium content represents a significant improvement over the prior art which can be achieved without a substantial increase in resources and cost-effectively.

USE EXAMPLE D

Test of Application

Sample preparation: In a mixer

| | |
|---|---|
| 100 | parts of LLDPE (linear low density polyethylene, Mitsubishi F-30FG-N) powder |
| 0.07 | part of sterically hindered phenol (Irganox 1076) and |
| 0.075, 0.10 or 0.125 | part of the relevant stabilizer | are mixed together in the dry state and homogenized in a Collin single-screw extruder initially at 210° C. and then, after granulation, in a Göttfert Extrusiometer (compression 1:3, 70 min$^{-1}$) extruded a total of five times at 240° C. and granulated. After the first, third, and fifth passage, the melt flow index (MFI) is determined each time (Zwick, 190° C., 2.16 kg). The results obtained are summarized below.

| MFI [g/10 min] | Conc. [phr] | Product 1 | Product 2 | Comparison product |
|---|---|---|---|---|
| 1$^{st}$ passage | 0.075 | 1.00 | 0.99 | 0.98 |
| | 0.100 | 0.99 | 0.97 | 0.98 |
| | 0.125 | 0.98 | 0.98 | 0.98 |
| 3$^{rd}$ passage | 0.075 | 0.93 | 0.94 | 0.91 |
| | 0.100 | 0.97 | 0.99 | 0.99 |
| | 0.125 | 0.99 | 0.99 | 0.98 |
| 5$^{th}$ passage | 0.075 | 0.74 | 0.76 | 0.70 |
| | 0.100 | 0.93 | 0.97 | 0.87 |
| | 0.125 | 0.94 | 0.97 | 0.82 |

The products 1 and 2 of the invention equally show an improved stabilizing action compared with the comparison product, in particular with high demands being placed on the stabilizer action, expressed by an MFI value which is as high (LLDPE is mainly degraded by cross-linking, leading to low MFI-values) and as unchanged as possible, especially after the 5th extrusion passage.

USE EXAMPLE E

Test of Application

Sample preparation: In a mixer 100 parts of PP (polypropylene, Solvay Polyolefins Eltex P HL 001PF) powder 0.05 parts of sterically hindered phenol (Irganox1010) and 0.04 resp.
0.07 parts of the relevant stabilizer
are mixed together in the dry state and homogenized in a Collin single screw extruder initially at 210° C. and then, after granulation, in a Göttfert Extrusiometer (compression 1:3, 50 min$^{-1}$) extruded a total of five times at 270° C. and granulated. After the first, third and fifth passage, the melt flow index (MFI) is determined each time (Zwick, 230° C., 2.16 kg). The results obtained are summarized below

| MFI [/10 min], 0.04 parts of stabilizer | Product 2 | Product 7 | Comparison product |
|---|---|---|---|
| 1$^{st}$ passage | 3.17 | 3.48 | 4.34 |
| 3$^{rd}$ passage | 4.61 | 5.83 | 8.80 |
| 5$^{th}$ passage | 7.22 | 10.20 | 15.10 |

| MFI [/10 min], 0.07 parts of stabilizer | Product 2 | Product 7 | Comparison product |
|---|---|---|---|
| 1$^{st}$ passage | 2.58 | 2.75 | 2.81 |
| 3$^{rd}$ passage | 2.80 | 3.72 | 4.15 |
| 5$^{th}$ passage | 3.76 | 4.62 | 6.11 |

The products 2 and 7 equally show improved stabilizing action compared to the comparison product, in particular with high demands being placed on the stabilizer action, expressed by an MFI-value which is as low (PP is degraded by chain scission, leading to high MFI-values) and as unchanged as possible, especially after the 5$^{th}$ extrusion passage.

The stabilizing effect is found to be concentration-independent, i.e. not limited to a small concentration range and the results show that the stabilizers prepared according to the invention have a markedly improved specific stabilizing action in various polymers compared with the prior art (Comparison Product).

What is claimed is:

1. A phosphonite or phosphinite of general formula (I)

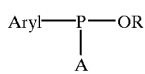

(I)

where
aryl is a substituted or unsubstituted aryl or heteroaryl radical;
R is any organic radical having 5–36 carbon atoms, which can also contain hetero atoms; and
A is either R or OR,
prepared by reacting a Friedel-Crafts reaction product of general formula (II)

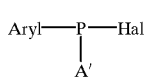

(II)

where
aryl has the meaning above;
Hal is halogen; and
A' is either Hal or R,
with a hydroxyl compound of the formula (III)

  (III)

where
R has the meaning above,
separating off a majority of insoluble byproducts formed during the reaction, characterized in that an aftertreatment is carried out wherein the aftertreatment comprises:
adding
  a) a protic compound selected from the group consisting of alcohols, ammonia, primary amines, secondary amines and water, or
  b) an oxide, hydroxide, (hydrogen)carbonate or (hydrogen)phosphate of a metal, or
  c) a nitrogen containing compound selected from the group consisting of carbonic acid amides, thiocarbonic acid amides, carbonic acid imides, thiocarbonic acid imides, lactames, thiolactames, carbonic acid hydrazides, urea, thiourea, symmetrically and asymmetrically substituted urea and thiourea derivatives, urethanes, uretimides, guanidine and its salts and melamine and derivatives thereof, including polymeric compounds of all named classes, or
  d) any combination of one or more of the compounds of a) to c),
wherein the addition of a) to d) is carried out in the absence of a solvent or in an inert, nonpolar solvent, and separating off resulting byproducts from the reaction mixture, wherein the phosphonite or phosphinite is characterized by a content of chloride or hydrolysable chlorine, determined by argentometric titration, of less than 0.5%.

2. A phosphonite or phosphinite of general formula (I)

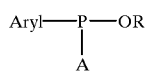

(I)

where
aryl is a substituted or unsubstituted aryl or heteroaryl radical;
R is any organic radical having 5–36 carbon atoms, which can also contain hetero, atoms; and
A is either R or OR,
prepared by reacting a Friedel-Crafts reaction product of general formula (II)

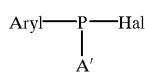

(II)

where
aryl has the meaning above;
Hal is halogen; and
A' is either Hal or R,
with a hydroxyl compound of the formula (III)

  (III)

where
R has the meaning above,
separating off a majority of insoluble byproducts formed during the reaction, characterized in that an aftertreatment is carried out wherein the aftertreatment comprises:
adding
  a) a protic compound selected from the group consisting of alcohols, ammonia, primary amines, secondary amines and water, or b) an oxide, hydroxide, (hydrogen)carbonate or (hydrogen)phosphate of a metal, or
c) a nitrogen containing compound selected from the group consisting of carbonic acid amides, thiocarbonic acid amides, carbonic acid imides, thiocarbonic acid imides, lactames, thiolactames, carbonic acid hydrazides, urea, thiourea, symmetrically and asymmetrically substituted urea and thiourea derivatives, urethanes, uretimides, guanidine and its salts and melamine and derivatives thereof, including polymeric compounds of all named classes, or
d) any combination of one or more of the compounds of a) to c), wherein the addition of a) to d) is carried out in the absence of a solvent or in an inert, nonpolar solvent, and separating off resulting byproducts from the reaction mixture, wherein the phosphonite or phosphinite is characterized by an aluminium content less than 500 ppm, determined by the AES/ICP method.

3. The phosphonite according to claim 1 which is a reaction product of 2,4-di-tert-butylphenol with the Friedel-Crafts reaction product of diphenyl and phosphorus trichloride.

4. The phosphonite according to claim 2, which is a reaction product of 2,4-di-tert-butylphenol with the Friedel-Crafts reaction product of diphenyl and phosphorus trichloride.

* * * * *